United States Patent [19]

Fischer

[11] Patent Number: 5,098,299
[45] Date of Patent: Mar. 24, 1992

[54] COMPOSITIONS AND METHODS FOR REPAIRING AND SEALING RUBBER DAMS AND ISOLATING TISSUE

[75] Inventor: Dan E. Fischer, Salt Lake City, Utah

[73] Assignee: Ultradent Products, Inc., Salt Lake City, Utah

[21] Appl. No.: 378,596

[22] Filed: Jul. 11, 1989

[51] Int. Cl.$^5$ .............................................. A61K 6/08
[52] U.S. Cl. .............................. 433/215; 433/199.1; 106/31
[58] Field of Search ................ 433/215, 199.1; 106/31

[56] References Cited

PUBLICATIONS

Orabase ® Plain (Product), Colgate-Hoyt Laboratories, Canton, MA.
Orabase ®-B with Benzocaine (Product), Colgate-Hoyt Laboratories, Canton, MA.

Primary Examiner—V. Millin
Attorney, Agent, or Firm—Workman, Nydegger & Jensen

[57] ABSTRACT

A sealing or barrier forming putty caulk of the present invention contains polydimethylsiloxane to provide adhesive and hydrophobic characteristics. The sealing or barrier forming putty caulk also contains propylene glycol in sufficient amounts to provide the composition with hydrophilic properties so the compound will adhere to wet, as well as dry, surfaces or tissue. The sealing or barrier forming composition also contains carboxymethylcellulose to assure that the compound has a homogeneous blend of the ingredients. The sealing or barrier forming composition also contains inert fillers and possibly trace amount of a surfactant.

The methods of using the sealing or barrier forming compound of the present invention include delivering the compound efficiently and accurately to the subject region through a syringe. The method of shaping, forming, molding, spreading and rubbing the composition into the desirable configuration in a variety of applications is also set forth to improve the art of dental procedures for the repair of rubber and other dental dams or when procedures require isolating certain tissues, objects or regions as dictated by the dental procedure.

The composition and methods of using the present invention include applying and using the composition as a bland bandage to shield and protect irritated, diseased, ulcerated or lesioned tissue.

60 Claims, 1 Drawing Sheet

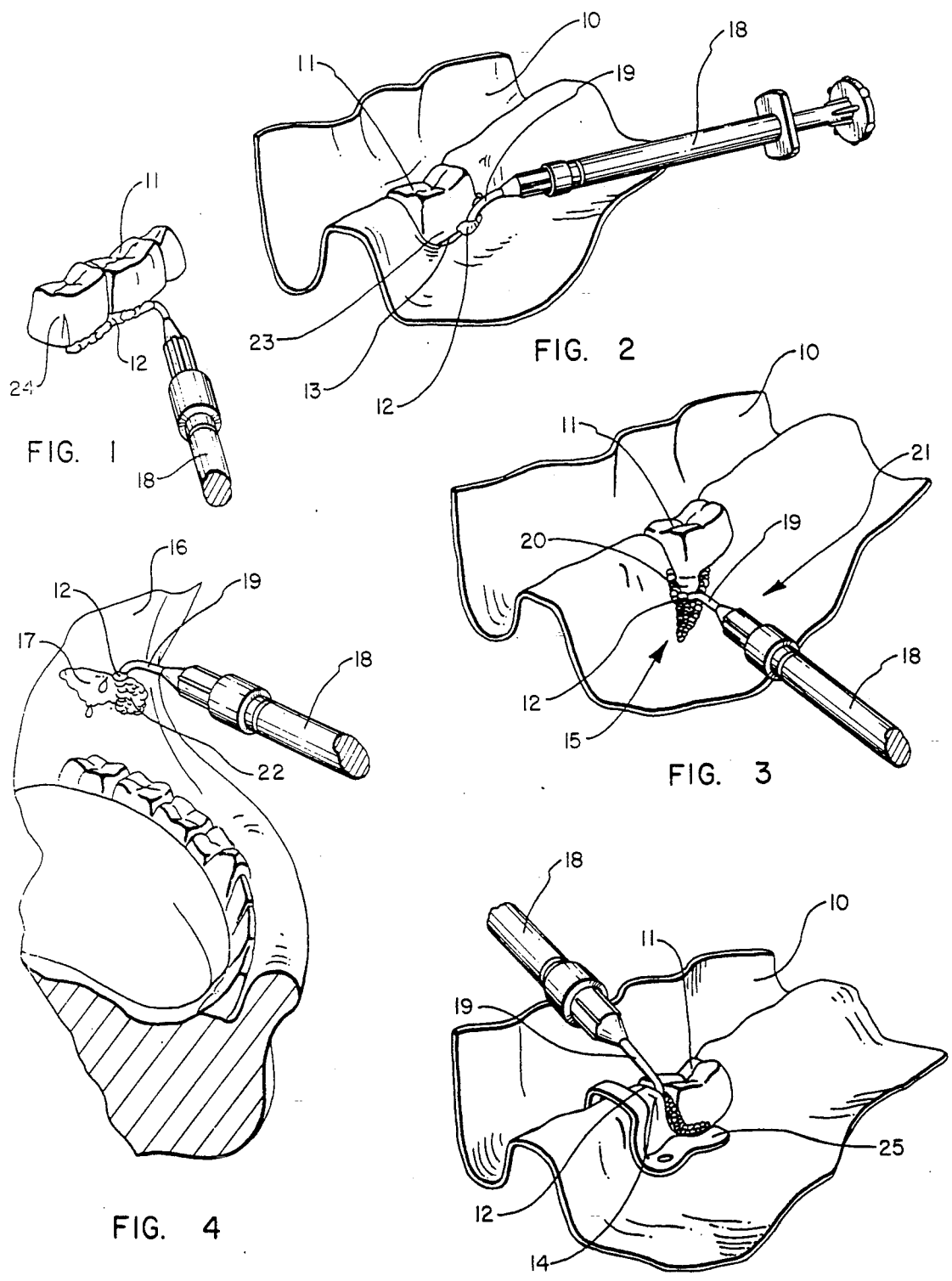

COMPOSITIONS AND METHODS FOR REPAIRING AND SEALING RUBBER DAMS AND ISOLATING TISSUE

BACKGROUND

1. The Field of the Invention

The present invention relates to compositions and methods for using these compositions for sealing, repairing, or augmenting rubber dams used in dental procedures. In addition, the present invention has application in isolating tissues or teeth during dental procedures or even for isolating or protecting other tissue by functioning as a bland bandage. More particularly, the present invention relates to specially designed putty caulk and bandage compositions. The putty caulk compositions of the present invention are known to be biocompatible and safe, being sufficiently hydrophilic that the compositions adhere to wet tissue while at the same time being sufficiently elastomeric, durable, and hydrophobic that they resist becoming deformed, deteriorated, or washed away.

2. The Prior Art

Prior art substances, referred to as coating pastes, are used to promote healing of wet tissue by protecting against further irritation resulting from cankers, mouth ulcers or lesions, dental procedures, dental or orthodontic appliances and denture irritation, oral surgery, and other mouth or gum sores.

The coating pastes are useful in coating the irritated area to provide a type of protective barrier for the irritated tissue to prevent further irritation or aggravation. Some coating pastes provide temporary relief and comfort to localized irritations or injuries through the use of local anesthetics.

Oral coating pastes are often applied to tissue whose surface is dynamic. Some currently available coating pastes embrace compositions which are not capable of adequately recovering size and shape after deformation caused by the dynamic nature of the underlying tissue. This is particularly important in conjunction with the use of a coating paste on any body region which extends, bends, or otherwise moves in such a manner that the surface is in some way distorted. While skin and other tissue is capable of being stretched or expanded and thereafter resuming its former shapes, some conventional coating pastes cannot.

Currently available coating pastes have little or no utility in conjunction with the sealing, repairing, or augmenting of rubber dams used in dental procedures. They have been developed as compounds to coat ulcerated or lesioned tissue to provide some comfort and protection against irritation. The prior art coating pastes were not designed to seal, repair, or augment wet and/or dry rubber dams and other dental appliances. To the contrary, the application of currently available coating pastes focuses upon their application to irritated or diseased tissue. What is needed is a compound which adheres to wet and dry rubber dams, dental appliances and other prostheses to aid the dental professional in dental procedures.

Currently available coating pastes lack elastomeric properties essential to a continued conformance to the surface of the tissue to which it is applied. Because the resilience of many types of tissue is not paralleled by resilient coating pastes, the present coating pastes lack the ability to adequately remain in contact with or attached to the tissue when the tissue is stressed or otherwise deformed. In order for the coating paste to be most effective, it is important that the coating paste remain attached to, in contact with, and deform with the tissue, yet still be able to return to its former shape relative to the tissue before deformation.

Because the present coating pastes are not meant to be a permanent application or prostheses, over time they erode, are wiped or scraped off, or are spread by water and saliva. It is, therefore, necessary from time to time to reapply or readminister the coating paste. Because it is not always possible to clean and prepare the tissue for each application of coating paste, it is essential that the protective coating paste be able to bond to itself so that subsequent applications of the coating paste serve as a perpetual seal or barrier providing continuing protection.

While currently available coating pastes tend to retain enough of their natural moisture such that, upon reapplication of the coating paste, the former application readily bonds with the reapplication, reapplication of coating pastes has practical limitations attributable to the characteristics of the compounds themselves. Reapplication or layering of coating pastes is limited by the ability of the coating paste to withstand contact with foreign articles. Coating pastes are subject to ready deterioration of body mass and shape upon contact, thereby suffering alteration and loss of mass and dimension. This is a result of the viscous characteristics of the coating paste compounds. What is needed is a compound whose mass and dimensions are less affected by contact with fluids and foreign articles. This would result in less frequent reapplication because the integrity of the reapplication would not be readily diminished by contact with fluids and other foreign articles. What is needed is a heavier paste which will layer and augment the dimensions of the application without being subject to immediate deterioration.

Furthermore, in some circumstances, it is desirable that the injured or irritated area not be reexposed. It is, therefore, important to have a continual seal or barrier. If the coating paste of reapplication blends into the coating paste of a prior application, a perpetual barrier is formed. This is important to effectuate continued protection or comfort to the user.

In various dental procedures, it is important to have the aid of a compound which adheres equally to hard or soft tissue, as well as wet and dry tissue. The presently available coating pastes are not designed to act as an extension of dental appliances, or to seal, repair or augment rubber dams, and the like, but are designed to shield irritated moist tissue. What is needed is a compound which may be applied to a rubber dam or other object, whether hard or soft, wet or dry, or to any nature of tissue for universal application in dental procedures. Similarly, a dental compound should be equally effective when applied to teeth and bones as it is when applied to gums or mucosal tissue, or to skin or muscle.

In many dental procedures, a variety of different tissues and objects interact and are in close proximity to one another. In some dental procedures it is necessary to form an effective barrier between or seal together two very different types of tissue and materials. The currently available coating pastes are not designed to be a seal or barrier between distinct types of materials such as a rubber dam and a gum or tooth. What is needed is a compound which is equally effective to seal and/or repair rubber dams and other dental appliances without being harmful to adjacent tissue. Such a compound would permit the dental professional to readily apply the compound to areas where dissimilar tissue and objects meet one another, such as tooth, gum, and rubber dam to isolate or seal the area, thereby providing a clean and dry field for the dental procedure.

Similarly, a dental compound should readily attach to dental appliances and prostheses whether metal, plastic, rubber, or ceramic. Particularly in the case of a rubber dam, for example, if a rubber dam is employed to isolate a subject tooth or crown to prevent harmful substances from contacting tooth, crown or gum, or to provide a clean and dry field for the dental procedure, and if the rubber dam is unable to effectively seal the base of the tooth or crown because of gaps or other irregularities in the surface of the tooth or crown, some sort of seal is needed to seal or fill voids between the rubber dam and tooth or crown. Similarly, some sort of seal is needed to seal or fill gaps between any other objects and oral tissue.

It is also not uncommon for a rubber dam to tear or become punctured during the course of dental activities. A repair or sealing compound is needed which adheres to the rubber dam and has sufficient elastomeric properties to effectively repair tears or punctures and permit the dental professional to continue the procedure without having to clean the area, remove the rubber dam, again prepare the tooth or crown to receive a rubber dam, and again apply a rubber dam to isolate or seal the tooth or crown. Such inconvenience presently causes increased time and expense of the procedure. To the contrary, the dental expert with an effective sealing or repair compound could merely apply a hydrophobic, yet sufficiently hydrophilic, resilient caulk to the damaged rubber dam and continue the procedure to conclusion. This ease of repair and convenience is, however, not possible with the currently available coating paste compositions.

One very important property of a dental compound for use in sealing, repairing, or isolating dental tissue, prostheses or appliances during dental procedures is that the compound be capable of affixing itself to the surface of wet or dry tissue, prostheses, or dental object.

Whether mucosal, gingival, pulpal, enamel, epidural, or any other tissue or surface, a dental compound's effectiveness is directly related to its ability to adhere to wet or dry tissue or objects. For example, in order to seal a rubber dam to a gum or a tooth, the affinity of the compound to both types of surfaces dictates its convenient, practical, and effective use. It is, therefore, important that the dental compound or paste adhere equally well to wet, as well as dry, surfaces.

Some cements have been used to provide clean and dry fields for endodontic procedures. One problem with the currently available cements which have been suggested for use in certain sealing procedures around teeth in endodontic procedures is that such cements are designed to chemically set and harden into a firm, cohesive unit, thereby making it difficult to remove it from relatively inaccessible cavities and openings. If the cement sets up hard over time and becomes difficult to remove, this increases extraction, cleanup, and preparation time for the dental or other professional. What is needed is a sealing compound that does not set up hard in the time in which the user is completing his procedure, but remains sufficiently pliable and workable to ensure easy application, reapplication if necessary, extraction or removal when needed.

The surface of the tissue with which the coating paste has contact is often subject to tensile forces of bending, twisting, or expansion. Tension is the death knell to unreinforced compositions causing cracks, fractures, and fragmentation of the integrity of the structure. Therefore, it is important that the coating paste not become brittle or otherwise loose its unitized mass structure and thus be subject to destructive tensile or flexural forces. Brittle compositions have little, if any, tensile strength. As a result, if the coating paste becomes brittle or looses its unitized mass and becomes subject to tensile or flexural forces. It is very important that the coating paste not crumble or deteriorate when subject to tensile or flexural forces.

Similarly, some coating pastes tend to curl at the edges as the coating pastes experiences various dynamic forces. It is important that the integrity of the coating paste's contact with the tissue not be compromised at its boundaries. A weakening or vulnerability of the seal or barrier at the edges lends to increased deterioration or erosion of the overall barrier. What is needed is a dental compound or caulk whose composition permits the compound to be spread to an edge, or even flared or tapered to the surface of the tissue, but whose compositions are not subject to detachment at the boundaries of the application such that the barrier or seal is threatened by pulling away or loosening of the compound from the tissue at the boundaries of the putty caulk application.

A principle feature of an effective putty caulk for sealing, repairing, or isolating dental tissue, prostheses in appliances during dental procedures is that a putty caulk remain in place to protect, seal, or otherwise separate tissue and or other objects. A very significant feature of an effective protective putty caulk is, therefore, that the compositions of the putty caulk be sufficiently hydrophobic so as to resist being washed away by saliva, rinsing or other body fluids shortly after application.

Because the caulk compound may be necessary in a variety of cavities, voids, cracks, holes, tears, and the like, it is important that compound caulk be sufficiently malleable, pliable, and viscous such that the compound be readily shaped, formed, molded, spread, rubbed, injected or otherwise delivered into the required location, shape, or configuration without cumbersome preparation or procedure.

If the user must treat, mix, knead, thicken, or otherwise further prepare the compound for its intended use, the relevant procedures are complicated and their duration lengthened. Similarly, if the compound must be applied in only a certain manner, such as dabbing with a compound rich swab, small, remote or hard-to-reach regions may not be properly serviced by the compound. The effectiveness of the resultant seal or barrier may be directly related to the ability to form, shape, or otherwise deliver the compound to the particular tissue to meet the particular needs of the subject tissue or its surface.

It is, therefore, important that a putty caulk be developed which is capable of readily adapting to various methods of administration and delivery while producing the desired seal or barrier without effecting the convenience of its use or the comfort of the receiving patient or ultimate user.

Another important feature of an effective putty caulk is the ability to apply the putty caulk to the tissue or object notwithstanding the immediate environment. A good example is the necessity of applying the putty caulk while the tissue or object is actually submerged. Many coating pastes are not amenable to administration to submerged tissue. Some sealing cements actually require a dry field before application will be successful. In some circumstances, it may be not only convenient, but necessary, to apply the putty caulk to tissue or articles submerged under water or saliva.

For obvious reasons such as time, cost, convenience, and cleanliness, it is advantageous to repair a leaking rubber dam quickly during the dental procedure rather than be required to stop the procedure, remove the rubber dam, clean the site, place another rubber dam, and then continue with the dental procedure. Instead, it would be much more cost effective for the dental professional and require less treatment time for the patient if the rubber dam can be effectively repaired or plugged so that the procedure may continue relatively uninterrupted in the presence of the various fluids attendant to the procedure at hand.

From the foregoing. it will be appreciated that what would be needed in the art are improved putty caulk compositions which exhibit elastomeric properties and characteristics which respond resiliently to the dynamic forces exerted upon the putty caulk by the underlying rubber dam, tissue or other object.

It would be further improvement in the art to provide a compositions of putty caulk which will bond and blend to itself to form a perpetually uniform seal or barrier notwithstanding the passage of time.

Additionally, it would be an enhancement in the art for a putty caulk to adhere equally effectively to hard and soft tissue. The interaction or interfacing of different types of tissue require the universal application of the same putty caulk to all types of tissue.

Similarly, it would be an enhancement of the art for a putty caulk to adhere to rubber dams and other dental prostheses, objects, and orthodontic appliances as effectively as it adheres to dry natural tissue. The interaction or interfacing of these artificial objects with naturally occurring tissue require the universal application of the same putty caulk to all types of tissue and metal, plastic, rubber or ceramic materials.

It would also be an enhancement of the art that the putty caulk adhere equally effectively to wet, as well as dry tissue or objects. Because some tissue and objects are not dry by nature and cannot be sufficiently dried before application of a putty caulk, the putty caulk must be sufficiently hydrophilic as to readily attach itself to moist tissue or objects, while simultaneously being sufficiently hydrophobic to resist being washed or rinsed away.

It would furthermore be an advancement in the art to provide a putty caulk that is sufficiently elastomeric which, however, does not set up so hard over time that it is difficult to efficiently and economically clean, remove or replace.

Similarly, it would be an improvement in the art to provide a putty caulk which does not crumble under the normal tensile forces exerted upon the putty caulk over time by the underlying rubber dam, tissue or other object.

It would be a significant improvement in the art to provide a putty caulk which does not curl or otherwise deform over time within its mass or at its boundaries but remains in contact with the underlying tissue or object to maintain the integrity of the seal or barrier at it borders.

It would, in addition, be an improvement in the art to provide a putty caulk which in conjunction with its elastomeric characteristics and properties is also sufficiently malleable, pliable, and has sufficiently high viscosity and working properties to permit the user to shape, form, mold, spread, rub, dab, inject, or otherwise deliver the putty caulk to the subject region in a form suitable to create an effective seal or barrier.

It would be an improvement in the art to provide compositions of putty caulk and methods for successfully applying said putty caulk to submerged or inundated tissue or objects.

The foregoing, and other features and objects of the present invention are realized in the compositions and methods for sealing or repairing rubber dam and other dental implements, or for protecting irritated tissue with a bland bandage.

BRIEF SUMMARY AND OBJECTS OF THE INVENTION

The present invention is directed to compositions and methods for repairing or sealing rubber dams and for otherwise isolating tissue from harmful contact or irritation. A primary component of the putty caulk compositions of the present invention is a combination silicone-glycol base.

The silicone base provides necessary hydrophobic properties to the putty caulk of the present invention. Hydrophobic properties aid the putty caulk in resisting being washed or rinsed away. Some silicone is biocompatible, and, therefore, does not irritate or damage natural tissue or artificial dental apparatus. The preferred silicone of the present invention is polydimethylsiloxane.

Another primary component of the putty caulk compositions of the present invention is the presence of a hydrophilic material. Hydrophilic properties aid the putty caulk in adhering to wet surfaces. Many glycol compounds are hydrophilic and biocompatible and, therefore, do not irritate or damage natural tissue or artificial dental apparatus. The preferred glycol of the present invention is propylene glycol.

The putty caulk compositions of the present invention also contain a filler material. The filler material functions to properly suspend the composition's substituents and prevent balling-up of the compound. The preferred filler is carboxymethylcellulose. Practice of the invention has also revealed that cellulose materials also contribute to the hydrophilic nature of the present invention.

Other inert fillers are added to obtain desired physical properties including, but not limited to, viscosity and texture. Inert fillers such as glass sphere aid the putty caulk in resisting mechanical abrasion and deformation from external forces against the surface of the putty caulk.

In addition, the compositions may contain coloring or pigment agents, opacifiers, benzocaine or other local anesthetics, light curing agents, base catalyst curing agents, water catalyst curing agents, and other components which may be optionally desirable for a given putty caulk composition or application.

It is, therefore, an object of the present invention to provide compositions and methods of a putty caulk for repairing, sealing, or augmenting rubber dams and other dental appliances.

It is another object of the present invention to provide methods and compositions for a putty caulk which alone or in conjunction with other dental apparatus or appliances provides a clean and dry field for dental procedures.

It is also an object of the present invention to provide compositions and methods of a putty caulk for isolating tissue from harmful contact or irritation.

A further objective of the present invention is to provide putty caulk compositions which are sufficiently hydrophobic so as to resist being washed away by any fluid medium.

Still another objective of the present invention is to provide putty caulk compositions which are sufficiently hydrophilic so as to adhere to wet as well as dry tissue.

An object of the present invention is to provide putty caulk compositions which are sufficiently hydrophobic so as to resist being washed away by any fluid medium while at the same time are sufficiently hydrophilic so as to adhere to wet as well as dry tissue.

Yet another objective of the present invention is to provide compositions of putty caulk and methods for successfully applying said putty caulk to submerged or inundated tissue or objects.

Another objective of the present invention is to provide improved putty caulk compositions which exhibit elastomeric properties and characteristics which respond resiliently to the dynamic forces exerted upon the putty caulk by the underlying rubber dam, tissue or other dental object.

A further objective of the present invention is to provide compositions of putty caulk which will bond and blend to itself to form a uniform seal or barrier.

Another object of the present invention is to provide putty caulk compositions which adhere to both hard and soft dental appliances and tissue.

Another object of the present invention is to provide putty caulk compositions which adhere to both wet and dry dental appliances, such as rubber dams, and tissue.

An additional objective of the present invention is to provide putty caulk compositions which effectively adhere to dental prostheses, objects, and orthodontic appliances, because they often interact or interface with naturally occurring tissue requiring the universal application of the same putty caulk compositions to all types of naturally occurring tissue and metal, plastic, rubber or ceramic materials.

A further objective of the present invention is to provide putty caulk compositions that do not set up hard, but remain easily removable, cleanable, or replaceable in an efficient and economic manner.

Yet another objective of the present invention is to provide putty caulk compositions which do not crumble under the normal tensile or flexural forces exerted over time upon the putty caulk by the underlying tissue or object or by external forces.

An additional important objective of the present invention is to provide putty caulk compositions which do not curl or otherwise deform over time at its boundaries, but remains in contact with the underlying tissue or object to maintain the integrity of the seal or barrier.

Another objective of the present invention is to provide putty caulk compositions which, in conjunction with elastomeric characteristics and properties, are also sufficiently malleable and pliable enough to permit the user to shape, form, mold, spread, rub, dab, inject or otherwise deliver putty caulk compositions to the subject region in a form suitable to create an effective seal or barrier, and in a manner which saves valuable time and expense during the dental procedure.

These and other objects and features of the present invention will become more fully apparent from the description which follows, or may be learned by the practice of the invention.

BRIEF DESCRIPTION OF THE DRAWINGS

FIG. 1 is a general view of a putty caulk composition being delivered by a syringe to the base of a tooth or crown to form a sealing seat in preparation for receiving a rubber dam.

FIG. 2 is a general view of a putty caulk composition being delivered by a syringe to seal gaps or voids between a rubber dam and the base of a tooth or crown after the rubber dam is seated in putty caulk as shown in FIG. 1.

FIG. 3 is a general view of a putty caulk composition being delivered by a syringe to seal or repair a tear or puncture in a damaged rubber dam.

FIG. 4 is a general view of the putty caulk composition as applied to the mucosal tissue of mouth, gum or tongue.

FIG. 5 is a general view of the putty caulk composition as applied to complete a seal on the abutment tooth of a fixed bridge with a rubber dam when necessary for root canal treatment.

DETAILED DESCRIPTION OF THE PREFERRED EMBODIMENTS

As summarized above, the present invention relates to compositions and methods for repairing and sealing rubber dams to isolate tissue from harmful contact or irritation and to provide or maintain a clean and dry field for dental procedures. The putty caulk compositions within the scope of the present invention not only act to repair and seal rubber dams and other artificial dental instruments and apparatus, but also act to isolate such items from natural tissue. The putty caulk compositions within the scope of the present invention also serve as a bland bandage to provide a barrier shielding sensitive or irritated tissue from the discomfort or aggravation associated with contacting other tissue or fluids.

During the course of dental procedures, there are times when the use of a rubber dam is necessary to isolate or shield certain areas of the mouth. This is particularly important when the use of caustic, toxic, or otherwise harmful materials threaten other tissue or objects associated with the locale. For example, when a vital bleaching procedure is being performed, toxic peroxide solutions must be used. Strong peroxide is extremely harmful to gingiva and other soft tissue.

In an effort to isolate the area which is to come in contact with the peroxide, the dental professional will employ a rubber dam or the like in order to control the extent to which peroxide comes in contact with any tissue in the hopes that peroxide only comes in contact with the target tissue. FIG. 1 represents how the dental professional may prepare the base of a tooth or crown 11 by applying a bead 24 of the putty caulk to form a seat into which the thereafter placed dental or rubber dam may seat in establishing a seal. FIG. 2 illustrates how a rubber dam 10, in conjunction with the putty caulk, serves to isolate a tooth or crown 11, and other underlying tissue. The rubber dam is seated in bead 24 of FIG. 1, and putty caulk 12 is delivered to void 13 between the dental or rubber dam 10 and the tooth or crown 11.

However, when the rubber dam is put in place, there are circumstances in which the rubber dam 10 is unable to seal the base of the tooth or crown 11 or wrap all the way around a bridge connector 14 possibly even if a currently available coating paste is used. As shown in FIG. 5, clamp 25 attempts to seal the rubber dam around bridge connector 14. The seal is, however, incomplete at best. In such a case, the attempt to isolate sensitive tissue threatened by the peroxide or hydrofluoric acid is incomplete.

Furthermore, when the rubber dam is set against or on tissue such as gingival tissue, the seal between the rubber dam and tissue is inadequate because the rubber dam typically seats on moisture/saliva coated tissue. This results in an inadequate seal between the rubber dam and the tissue. The putty caulk of the present invention serves to provide a better seal between the rubber dam and the tissue. A more effective seal is obtained if a layer or bead of putty caulk is disposed between the tissue and the rubber dam. FIG. 1 illustrates the preparation of base 23 of a tooth or crown 11 to provide a bead 24 of putty caulk into which a dental or rubber dam may seat. In the first instance, the hydrophilic nature of the putty caulk serves to establish an effective seal or bond between the moisture/saliva coated tissue and the putty caulk itself. Thereafter, the rubber dam is set into the putty caulk. Setting the rubber dam into the putty caulk establishes a second more effective seal or bond. In this way, the putty caulk acts as a sealing agent between the rubber dam and the threatened tissue.

Similarly, when it is necessary to undertake a procedure known as porcelain etching, the dental professional employs hydrofluoric acid. Just as it is important to keep toxic peroxides away from certain tissue, it is important to control the contact that hydrofluoric acid has with tissue and objects in the patient's mouth. A rubber dam is used to isolate tissue and to provide a clean and dry field for the dental procedure. Again, the putty caulk provides the sealing and repair convenience helpful to the dental professional.

In addition, if a rubber dam 10 is successfully placed, but due to other aspects of the procedure the rubber dam tears under stress, as illustrated at 15 in FIG. 3, or becomes punctured by some instrument or the like, or otherwise develops a leak, the isolation again becomes incomplete and other tissue may be threatened by the incomplete isolation of harmful substances or by contamination from moisture or saliva to the tooth or area to be restored. The putty caulk 12 of the present invention can be used to plug or seal such tears or punctures 15 to restore or maintain the clean, dry, and isolated field needed by the dental procedure.

Furthermore, if a region of mucosal tissue 16, as illustrated in FIG. 4, is subject to a canker, sore, lesion, abrasion 17, or is irritated for any reason, and it is necessary to shield that region from air, saliva or any other medium, an amount of the putty caulk 12 can be employed as a bland bandage. Lesioned tissue includes tissue in any state which causes discomfort such as diseased, distressed, aggravated, or sensitive tissue, and the like.

It is the purpose of the present invention to provide compositions capable of providing the requisite sealing and repair capabilities for augmenting or assisting rubber dams in isolating areas in which harmful or damaging substances are being used.

Similarly, the present invention serves as a bland bandage capable of shielding irritated or sensitive regions of mucosal tissue. The present invention may be applied directly to such tissue to isolate it from any contact which would interact with or otherwise aggravate the subject tissue.

A preferred putty caulk composition within the scope of the present invention contains a silicone-glycol base combined with a cellulose material, a surfactant, and inert fillers. More particularly, a preferred putty caulk composition within the scope of the present invention contains polydimethylsiloxane, propylene glycol, carboxymethylcellulose, inert fillers and a surfactant.

The preferred embodiment of the specially designed putty caulk compositions of the present invention has hydrophobic characteristics necessary to enable the compositions to resist being washed or swept away by other fluid mediums. Silicone-based materials are good examples of this type of substance. Silicone is practically insoluble in water and other fluids typically associated with mucosal tissue and other dental procedures. More, particularly, polydimethylsiloxane is the preferred substance to provide the hydrophobic properties of the present invention useful in the aqueous environment of the mouth of a patient.

Similar hydrophobic properties are exhibited by other silicone and silicone-like materials such as some urethane materials conducive to chemical and/or light curing processes which result in solid or semi-solid material. The present invention contemplates using light curing materials and processes in conjunction with the putty caulk or derivatives thereof.

Because the putty caulk compositions are usually or likely to be inundated by wet mediums, for example in the aqueous environment of the mouth, it is vital that the preferred embodiment not be eroded by fluids such as saliva, rinsing fluids, water jets, and fluids used in dental procedures. Therefore, one can use the putty caulk of the present invention because of the hydrophobic nature of the composition.

It is also important for the composition of the present invention to contain material(s) which provide the specially designed caulk compositions with adequate elastomeric properties which enable it to be resilient to deformation. Without such a property, the caulk compositions would not continue to adhere to the underlying tissue or object if stressed, extended, stretched, twisted or otherwise deformed, even after some period of time. In addition, the composition must be chemically bland to tissue. Again, the preferred material to serve this purpose is a silicone or silicone-like material such as some urethanes. More particularly, the preferred material is polydimethylsiloxane.

Elastomeric properties are useful to the dental professional because often the dental professional must isolate the target area or tissue without being able to immobilize the target area or tissue. Because the composition of the present invention exhibits adequate elastomeric properties, the specially designed caulk of the present invention will continue to adhere to and isolate the dynamic, underlying target area or tissue.

The preferred embodiment may have polydimethylsiloxane present in an amount ranging, by weight, from about 15% to about 60%. More typically, better results are obtained if polydimethylsiloxane exists in a range from about 18% to about 36%. Preferably, the polydimethylsiloxane component of the present invention should be present in an amount ranging from about 20% to about 30%. One source of the polydimethylsiloxane is Dow Chemical medical grade. Medical grade is useful because it is chemically bland and safe for use in conjunction with tissue and it adheres to latex and other rubber materials and dental appliances.

A preferred embodiment within the scope of the present invention will also contain properties which offer those hydrophilic properties necessary for the putty caulk compositions to adhere to wet surfaces in, for example, aqueous environments. Hydrophilic properties are important to the dental professional because they permit the dental professional to perform dam repair or plug leaks under the influence of water and other fluids without stopping the dental procedure to prepare the target area or tissue to receive the caulk compound. Glycols and glycol-like materials are the preferred substance to provide the hydrophilic properties. More particularly, propylene glycol is the most preferred substance.

It appears that the glycol component serves to more rapidly allow exposure of the cellulose component discussed below to the surface of the wet rubber dam or wet tissue to result in adhesion in a wet or submerged environment. The results are not as satisfactory absent propylene glycol. If the surface of the rubber dam or tissue is dry, albeit that the propylene glycol-cellulose interaction may offer some limited degree of adhesion, the adhesion to dry surfaces is greatly enhanced due to the glycol component.

Furthermore, propylene glycol exhibits an antibacterial effect by inhibiting the growth of mold. Mold thrives in a moist environment. Preventing the growth of mold is useful in sustaining the effective shelf life of the compound.

Propylene glycol may be substituted by ethylene glycol and glycerol and other water soluble, lower molecular weight glycols or glycol-like substances such as lower weight aliphatic glycols. These glycols also provide the necessary hydrophilic properties discussed above.

Propylene glycol provides satisfactory results when present in an amount ranging from about 0% to about 60%. Better results are obtained when the amount of propylene glycol present ranges from about 18% to about 36%. Preferably, propylene glycol should be present in an amount ranging from about 20% to about 30%.

Even though the range of propylene glycol extends to 0% on one end, that is not to say that glycol is not necessary for the preferred embodiment of the present invention. A putty caulk lacking glycol results in a caulk composition of limited utility. However, a putty composition lacking glycol is still superior to a putty caulk composition lacking the silicone component. Therefore, while the glycol component may be reduced to 0%, that is not to say that it does not contribute to the effectiveness of the putty caulk compound of the present invention. To the contrary, the glycol component is a member of the preferred embodiment of the present invention. In the absence of glycol, the desired hydrophilic character of the present invention is adequately maintained by the presence of cellulose offering satisfactory results, albeit not preferred results.

Practice of the invention has shown that compounds combining polydimethylsiloxane and propylene glycol in the ranges suggested result in satisfactory putty caulk compositions when combined with the other components discussed below. Preferable results are obtained, however, when the ranges of quantities of polydimethylsiloxane and propylene glycol vary somewhat inversely. That is, if the quantity of polydimethylsiloxane is increased, then preferably, the quantity of propylene glycol should be decreased. And conversely, if the quantity of polydimethylsiloxane is decreased, then preferably, the quantity of propylene glycol should be increased.

While it is well known that compounds containing different phases traditionally require an emulsifier to assist the compound in maintaining the desired homogeneous mixture of the components, the present invention is not dependent upon an emulsifier. In the presence of cellulose, inert fillers and with sufficient energy input upon mixing and blending, the resulting putty caulk compound is physically stable. Several cellulose materials have been employed with varying degrees of success. The preferred cellulose component is carboxymethylcellulose. More particularly, carboxymethylcellulose has proven superior over methylcellulose, hydroxypropylcellulose, or other cellulose materials, or like materials such as alginate, agars, and xanthan gums, in contributing to the desired consistency, viscosity, texture, or desired degree of adhesion of the compound to wet or moist surfaces. Carboxymethylcellulose serves satisfactorily when present in amounts ranging from about 10% to about 60%. More satisfactory results are obtained with the quantity of carboxymethylcellulose ranging from about 20% to about 55%. Preferably, carboxymethylcellulose should be present ranging from about 33% to about 45%.

The currently preferred embodiment also contains inert fillers to assist in bringing the putty caulk composition to a desirable texture and/or viscosity. The filler may be any solid material such as glass or plastic spheres or other similar materials known in the art. The filler could also be polypropylene or polymethylmethacrylate spheres, and the like.

More particularly, in the present preferred embodiment glass spheres are used as the inert filler. The glass spheres range in size from about 1 micron to about 40-50 microns depending upon the desired texture. The glass spheres function to fill the interstitial spaces of the composition and permit the texture and viscosity of the caulk composition to be altered by their addition. The desired texture/viscosity can be described as a putty caulk type material. To obtain maximum filling of interstitial spacing, it is suggested that two or more sizes of glass spheres be employed. The amount of filler added depends upon the effect it has upon the adhesive characteristics of the cellulose. The filler is added in such quantity so as not to compromise the adhesive contribution of the cellulose. For example, the silicone-glycol base is able to tolerate only a certain amount of solid material. If a certain viscosity above the optimum viscosity is desired, it requires replacing some solid, adhesive contributing cellulose with solid, viscosity influencing inert fillers. The natural result is a what appears to be a detrimental effect upon the adhesive properties of the overall putty caulk compound when an excessive amount of inert filler is employed.

The inert filler also provides the composition with the viscosity and consistency which permits the dental professional to work the putty caulk into the desired configuration by forming, molding, spreading, rubbing, or otherwise shaping the putty caulk to conform to the surface of the underlying contact surface as needed. A contact surface may be any tissue, dental dam or other dental appliance.

It has been found that some degree of wetting enhancement and/or aid to the homogeneity of the combination of the hydrophobic and hydrophilic components has been achieved in the presence of a surfactant. Any surfactant which enhances and/or aids the homogeneity of the combination of the hydrophobic and hydrophilic components may be employed. A preferred surfactant is a polysorbate surfactant. The preferred surfactant is Tween ® 60. Tween ® 60 may be substituted by other Tween ® polysorbate surfactants or other suitable non-ionic surfactants.

More particularly in the preferred embodiment of the present invention contemplates quantities of Tween ® 60 ranging from about 0.2% to about 10.0%. Preferably, the Tween ® 60 is present ranging from about 1.0% to about 6.0%. The percentage quantities of other surfactants will vary from surfactant to surfactant.

The currently preferred embodiment may also contain optional ingredients to serve various purposes. For example, the preferred embodiment may contain a coloring and opacifying agents to provide the putty caulk composition with the desired color or opaqueness. This can be very helpful to the dental profession. If the caulk composition is a color different than the surrounding target area or tissue, the distinction in color aids the dental professional in the application of the caulk composition by being able to ascertain whether the target area or tissue has been sufficiently blanketed with the caulk composition.

Similarly, if the caulk composition's color is distinguishable from that of a fluid contained by the rubber dam, it becomes readily apparent to the dental professional whether the dam is successfully containing or isolating the relevant fluid.

For the same reasons as discussed above, upon the removal of the caulk compound, it becomes immediately apparent to the dental professional whether the caulk compound has been satisfactorily removed.

The preferred embodiment may also contain a local anesthetic such as benzocaine, or the like, to provide local anesthetic effect to the applied region. Frequently, the target tissue or tissue adjacent to the target area of dental procedure experiences discomfort associated with the dental procedure. A local anesthetic is helpful to provide a numbing effect to mucous membranes, ulcerated tissue, and the like to alleviate pain and discomfort. The putty caulk of the present invention acts as a suitable carrier or vehicle for a local anesthetic.

EXAMPLES

The following examples set forth various putty caulk compositions within the scope of the present invention. However, the examples are merely illustrative of the present invention and are not intended to represent all embodiments within the scope of the present invention. All numbers expressed are weight percentages of the total composition, unless indicated otherwise.

EXAMPLE 1

A putty caulk composition within the scope of the present invention was prepared by combining 25.0% polydimethylsiloxane, 25.0% propylene glycol, 39.0% carboxymethylcellulose, 8.0% glass spheres having a size of approximately 1 to 40 microns, and 3.0% Tween ® 60 surfactant.

The composition ingredients were gradually blended together in the following manner to form a homogenous composition. The silicone, glycol, and surfactant were combined. The glass spheres were then added. Finally, the cellulose was added. This blending procedure is illustrative only and should not be deemed to be the required mixing procedure.

The foregoing procedure produced an elastomeric putty caulk composition which was sufficiently hydrophilic to adhere to wet or dry, hard or soft tissue, and was sufficiently hydrophobic to resist being washed away by external fluids. Furthermore, over a period of time from about 0.2 hours to about 4 hours, the putty caulk composition maintained clinically acceptable utilitarian properties.

EXAMPLE 2

A putty caulk composition within the scope of the present invention was made according to the procedure of Example 1, except that the ingredients were combined in the following amounts:

| Ingredients | Weight Percent |
| --- | --- |
| Polydimethylsiloxane | 29.8 |
| Propylene Glycol | 19.9 |
| Carboxymethylcellulose | 34.8 |
| Inert fillers | 9.9 |
| Tween ® 60 | 5.6 |

The foregoing procedure produced an elastomeric putty caulk composition which was sufficiently hydrophilic to adhere to wet or dry, hard or soft tissue, and was sufficiently hydrophobic to resist being washed away by external fluids. Furthermore, over a period from about 0.2 hours to about 4 hours, the putty caulk composition maintained clinically acceptable properties.

EXAMPLE 3

A putty caulk composition within the scope of the present invention is made according to the procedure of Example 1, except that the ingredients are combined in the following amounts:

| Ingredients | Weight Percent |
| --- | --- |
| Polydimethylsiloxane | 29.0 |
| Propylene Glycol | 21.0 |
| Carboxymethylcellulose | 39.0 |
| Inert fillers | 8.0 |
| Tween ® 60 | 3.0 |

The foregoing procedure produces an elastomeric putty caulk composition which is sufficiently hydrophilic to adhere to wet or dry, hard or soft tissue, and is sufficiently hydrophobic to resist being washed away by external fluids. Furthermore, over a period from about 0.2 hours to about 4 hours, the putty caulk composition maintains clinically acceptable properties.

EXAMPLE 4

A putty caulk composition within the scope of the present invention is made according to the procedure of Example 1, except that the ingredients are combined in the following amounts:

| Ingredients | Weight Percent |
| --- | --- |
| Polydimethylsiloxane | 21.0 |
| Propylene Glycol | 29.0 |
| Carboxymethylcellulose | 39.0 |
| Inert fillers | 8.0 |
| Tween ® 60 | 3.0 |

The foregoing procedure produces an elastomeric putty caulk composition which is sufficiently hydrophilic to adhere to wet or dry, hard or soft tissue, and is sufficiently hydrophobic to resist being washed away by external fluids. Furthermore, over a period from about 0.2 hours to about 4 hours, the putty caulk composition maintains clinically acceptable properties.

EXAMPLE 5

A putty caulk composition within the scope of the present invention is made according to the procedure of Example 1, except that the ingredients are combined in the following amounts:

| Ingredients | Weight Percent |
| --- | --- |
| Polydimethylsiloxane | 32.0 |
| Propylene Glycol | 18.0 |
| Carboxymethylcellulose | 39.0 |
| Inert fillers | 8.0 |
| Tween ® 60 | 3.0 |

The foregoing procedure produces an elastomeric putty caulk composition which is sufficiently hydrophilic to adhere to wet or dry, hard or soft tissue, and is sufficiently hydrophobic to resist being washed away by external fluids. Furthermore, over a period from about 0.2 hours to about 4 hours, the putty caulk composition maintains clinically acceptable properties.

EXAMPLE 6

A putty caulk composition within the scope of the present invention is made according to the procedure of Example 1, except that the ingredients are combined in the following amounts:

| Ingredients | Weight Percent |
| --- | --- |
| Polydimethylsiloxane | 19.0 |
| Propylene Glycol | 31.0 |
| Carboxymethylcellulose | 39.0 |
| Inert fillers | 8.0 |
| Tween ® 60 | 3.0 |

The foregoing procedure produces an elastomeric putty caulk composition which is sufficiently hydrophilic to adhere to wet or dry, hard or soft tissue, and is sufficiently hydrophobic to resist being washed away by external fluids. Furthermore, over a period from about 0.2 hours to about 4 hours, the putty caulk composition maintains clinically acceptable properties.

EXAMPLE 7

A putty caulk composition within the scope of the present invention is made according to the procedure of Example 1, except that the ingredients are combined in the following amounts:

| Ingredients | Weight Percent |
| --- | --- |
| Polydimethylsiloxane | 45.0 |
| Propylene Glycol | 5.0 |
| Carboxymethylcellulose | 39.0 |
| Inert fillers | 8.0 |
| Tween ® 60 | 3.0 |

The foregoing procedure produces an elastomeric putty caulk composition which is sufficiently hydrophilic to adhere to wet or dry, hard or soft tissue, and is sufficiently hydrophobic to resist being washed away by external fluids. Furthermore, over a period from about 0.2 hours to about 4 hours, the putty caulk composition maintains clinically acceptable properties.

EXAMPLE 8

A putty caulk composition within the scope of the present invention is made according to the procedure of Example 1, except that the ingredients are combined in the following amounts:

| Ingredients | Weight Percent |
| --- | --- |
| Polydimethylsiloxane | 15.0 |
| Propylene Glycol | 35.0 |
| Carboxymethylcellulose | 39.0 |
| Inert fillers | 8.0 |
| Tween ® 60 | 3.0 |

The foregoing procedure produces an elastomeric putty caulk composition which is sufficiently hydrophilic to adhere to wet or dry, hard or soft tissue, and is sufficiently hydrophobic to resist being washed away by external fluids. Furthermore, over a period from about 0.2 hours to about 4 hours, the putty caulk composition maintains clinically acceptable properties.

EXAMPLE 9

A putty caulk composition within the scope of the present invention is made according to the procedure of Example 1, except that the ingredients are combined in the following amounts:

| Ingredients | Weight Percent |
| --- | --- |
| Polydimethylsiloxane | 50.0 |
| Propylene Glycol | 00.0 |
| Carboxymethylcellulose | 39.0 |
| Inert fillers | 8.0 |
| Tween ® 60 | 3.0 |

The foregoing procedure produces an elastomeric putty caulk composition which is sufficiently hydrophilic due to the presence of cellulose to adhere to wet or dry, hard or soft tissue, and is sufficiently hydrophobic to resist being washed away by external fluids. Furthermore, over a period from about 0.2 hours to about 4 hours, the putty caulk composition maintains clinically acceptable properties.

EXAMPLE 10

A putty caulk composition within the scope of the present invention is made according to the procedure of Example 1, except that the ingredients are combined in the following amounts:

| Ingredients | Weight Percent |
|---|---|
| Polydimethylsiloxane | 30.0 |
| Propylene Glycol | 30.0 |
| Carboxymethylcellulose | 30.0 |
| Inert fillers | 7.0 |
| Tween ® 60 | 3.0 |

The foregoing procedure produces an elastomeric putty caulk composition which is sufficiently hydrophilic to adhere to wet or dry, hard or soft tissue, and is sufficiently hydrophobic to resist being washed away by external fluids. Furthermore, over a period from about 0.2 hours to about 4 hours, the putty caulk composition maintains clinically acceptable properties.

EXAMPLE 11

A putty caulk composition within the scope of the present invention is made according to the procedure of Example 1, except that the ingredients are combined in the following amounts:

| Ingredients | Weight Percent |
|---|---|
| Polydimethylsiloxane | 26.0 |
| Propylene Glycol | 38.0 |
| Carboxymethylcellulose | 25.0 |
| Inert fillers | 8.0 |
| Tween ® 60 | 3.0 |

The foregoing procedure produces an elastomeric putty caulk composition which is sufficiently hydrophilic to adhere to wet or dry, hard or soft tissue, and is sufficiently hydrophobic to resist being washed away by external fluids. Furthermore, over a period from about 0.2 hours to about 4 hours, the putty caulk composition maintains clinically acceptable properties.

EXAMPLE 12

A putty caulk composition within the scope of the present invention is made according to the procedure of Example 1, except that the ingredients are combined in the following amounts:

| Ingredients | Weight Percent |
|---|---|
| Polydimethylsiloxane | 36.0 |
| Propylene Glycol | 28.0 |
| Carboxymethylcellulose | 25.0 |
| Inert fillers | 8.0 |
| Tween ® 60 | 3.0 |

The foregoing procedure produces an elastomeric putty caulk composition which is sufficiently hydrophilic to adhere to wet or dry, hard or soft tissue, and is sufficiently hydrophobic to resist being washed away by external fluids. Furthermore, over a period from about 0.2 hours to about 4 hours, the putty caulk composition maintains clinically acceptable properties.

EXAMPLE 13

A putty caulk composition within the scope of the present invention is made according to the procedure of Example 1, except that the ingredients are combined in the following amounts:

| Ingredients | Weight Percent |
|---|---|
| Polydimethylsiloxane | 22.0 |
| Propylene Glycol | 22.0 |
| Carboxymethylcellulose | 45.0 |
| Inert fillers | 8.0 |
| Tween ® 60 | 3.0 |

The foregoing procedure produces an elastomeric putty caulk composition which is sufficiently hydrophilic to adhere to wet or dry, hard or soft tissue, and is sufficiently hydrophobic to resist being washed away by external fluids. Furthermore, over a period from about 0.2 hours to about 4 hours, the putty caulk composition maintains clinically acceptable properties.

EXAMPLE 14

A putty caulk composition within the scope of the present invention is made according to the procedure of Example 1, except that the ingredients are combined in the following amounts:

| Ingredients | Weight Percent |
|---|---|
| Polydimethylsiloxane | 32.0 |
| Propylene Glycol | 12.0 |
| Carboxymethylcellulose | 45.0 |
| Inert fillers | 8.0 |
| Tween ® 60 | 3.0 |

The foregoing procedure produces an elastomeric putty caulk composition which is sufficiently hydrophilic to adhere to wet or dry, hard or soft tissue, and is sufficiently hydrophobic to resist being washed away by external fluids. Furthermore, over a period from about 0.2 hours to about 4 hours, the putty caulk composition maintains clinically acceptable properties.

EXAMPLE 15

A putty caulk composition within the scope of the present invention is made according to the procedure of Example 1, except that the ingredients are combined in the following amounts:

| Ingredients | Weight Percent |
|---|---|
| Polydimethylsiloxane | 19.0 |
| Propylene Glycol | 16.0 |
| Carboxymethylcellulose | 54.0 |
| Inert fillers | 8.0 |
| Tween ® 60 | 3.0 |

The foregoing procedure produces an elastomeric putty caulk composition which is sufficiently hydrophilic to adhere to wet or dry, hard or soft tissue, and is sufficiently hydrophobic to resist being washed away by external fluids. Furthermore, over a period from about 0.2 hours to about 4 hours, the putty caulk composition maintains clinically acceptable properties.

EXAMPLE 16

A putty caulk composition within the scope of the present invention is made according to the procedure of Example 1, except that the ingredients are combined in the following amounts:

| Ingredients | Weight Percent |
|---|---|
| Polydimethylsiloxane | 15.0 |
| Propylene Glycol | 17.0 |
| Carboxymethylcellulose | 57.0 |
| Inert fillers | 8.0 |
| Tween ® 60 | 3.0 |

The foregoing procedure produces an elastomeric putty caulk composition which is sufficiently hydrophilic to adhere to wet or dry, hard or soft tissue, and is sufficiently hydrophobic to resist being washed away by external fluids. Furthermore, over a period from about 0.2 hours to about 4 hours, the putty caulk composition maintains clinically acceptable properties.

EXAMPLE 17

A putty caulk composition within the scope of the present invention is made according to the procedure of Example 1, except that the ingredients are combined in the following amounts:

| Ingredients | Weight Percent |
|---|---|
| Polydimethylsiloxane | 22.0 |
| Propylene Glycol | 35.0 |
| Carboxymethylcellulose | 34.0 |
| Inert fillers | 6.0 |
| Tween ® 60 | 3.0 |

The foregoing procedure produces an elastomeric putty caulk composition which is sufficiently hydrophilic to adhere to wet or dry, hard or soft tissue, and is sufficiently hydrophobic to resist being washed away by external fluids. Furthermore, over a period from about 0.2 hours to about 4 hours, the putty caulk composition maintains clinically acceptable properties.

EXAMPLE 18

A putty caulk composition within the scope of the present invention is made according to the procedure of Example 1, except that the ingredients are combined in the following amounts:

| Ingredients | Weight Percent |
|---|---|
| Polydimethylsiloxane | 44.0 |
| Propylene Glycol | 28.0 |
| Carboxymethylcellulose | 17.0 |
| Inert fillers | 8.0 |
| Tween ® 60 | 3.0 |

The foregoing procedure produces an elastomeric putty caulk composition which is sufficiently hydrophilic to adhere to wet or dry, hard or soft tissue, and is sufficiently hydrophobic to resist being washed away by external fluids. Furthermore, over a period from about 0.2 hours to about 4 hours, the putty caulk composition maintains clinically acceptable properties.

EXAMPLE 19

A putty caulk composition within the scope of the present invention is made according to the procedure of Example 1, except that the ingredients are combined in the following amounts:

| Ingredients | Weight Percent |
|---|---|
| Polydimethylsiloxane | 21.0 |
| Propylene Glycol | 27.0 |
| Carboxymethylcellulose | 39.0 |
| Inert fillers | 10.0 |
| Tween ® 60 | 3.0 |

The foregoing procedure produces an elastomeric putty caulk composition which is sufficiently hydrophilic to adhere to wet or dry, hard or soft tissue, and is sufficiently hydrophobic to resist being washed away by external fluids. Furthermore, over a period from about 0.2 hours to about 4 hours, the putty caulk composition maintains clinically acceptable properties.

EXAMPLE 20

A putty caulk composition within the scope of the present invention is made according to the procedure of Example 1, except that the ingredients are combined in the following amounts:

| Ingredients | Weight Percent |
|---|---|
| Polydimethylsiloxane | 32.0 |
| Propylene Glycol | 23.0 |
| Carboxymethylcellulose | 39.0 |
| Inert fillers | 3.0 |
| Tween ® 60 | 3.0 |

The foregoing procedure produces an elastomeric putty caulk composition which is sufficiently hydrophilic to adhere to wet or dry, hard or soft tissue, and is sufficiently hydrophobic to resist being washed away by external fluids. Furthermore, over a period from about 0.2 hours to about 4 hours, the putty caulk composition maintains clinically acceptable properties.

EXAMPLE 21

A putty caulk composition within the scope of the present invention is made according to the procedure of Example 1, except that the ingredients are combined in the following amounts:

| Ingredients | Weight Percent |
|---|---|
| Polydimethylsiloxane | 22.2 |
| Propylene Glycol | 30.2 |
| Carboxymethylcellulose | 39.0 |
| Inert fillers | 8.0 |
| Tween ® 60 | 0.6 |

The foregoing procedure produces an elastomeric putty caulk composition which is sufficiently hydrophilic to adhere to wet or dry, hard or soft tissue, and is sufficiently hydrophobic to resist being washed away by external fluids. Furthermore, over a period from about 0.2 hours to about 4 hours, the putty caulk composition maintains clinically acceptable properties.

EXAMPLE 22

A putty caulk composition within the scope of the present invention is made according to the procedure of Example 1, except that the ingredients are combined in the following amounts:

| Ingredients | Weight Percent |
| --- | --- |
| Polydimethylsiloxane | 21.0 |
| Propylene Glycol | 28.0 |
| Carboxymethylcellulose | 35.0 |
| Inert fillers | 8.0 |
| Tween ® 60 | 8.0 |

The foregoing procedure produces an elastomeric putty caulk composition which is sufficiently hydrophilic to adhere to wet or dry, hard or soft tissue, and is sufficiently hydrophobic to resist being washed away by external fluids. Furthermore, over a period from about 0.2 hours to about 4 hours, the putty caulk composition maintains clinically acceptable properties.

The putty caulk composition within the scope of the present invention is preferably used to repair, seal, or augment rubber dams. It may also be used to isolate tissue from harmful contact or irritation.

The preferred delivery of putty caulk composition 12 to the target tissue, as shown in FIGS. 1 to 5, is by means of a syringe 18 with delivery through a twist disposable White Mac ® tip or White Mini ® tip sold by Ultradent, Inc., Salt Lake City, Utah. The use of the syringe 18 permits the user to not only control the quantity of putty caulk composition 12 being applied to the targeted tissue but also permits accurate placement of putty caulk composition 12.

Putty caulk composition is preferably used when toxic materials necessitate an ideal seal to prevent toxic or harmful substances from contacting other tissue in procedures such as vital bleaching or porcelain etching. Putty caulk composition 12 is also preferably used for a seal on an abutment of a fixed bridge 14, for the difficult-to-obtain seal associated with rubber dams in conjunction with endodontics on compromised teeth and/or roots, for tears in damaged rubber dams 15 adjacent to teeth, fixed prostheses and/or soft tissue, for sealing isolated holes in rubber dams not adjacent to supporting soft tissue or teeth (e.g., in the lower lingual vestibule area), and for covering ulcerated, cankered or otherwise irritated tissue 17 as a bland bandage, as illustrated in FIG. 4.

While these examples of the use of the putty caulk composition of the present invention are the preferred uses, they are illustrative only. The present invention contemplates the use of the putty caulk composition on many types of tissue or objects requiring isolation or protection. The present invention may be used on many types of tissue including, for example, oral tissue, epithelial tissue, and potentially epidermal tissue. For example, the putty caulk composition of the present invention is also effective as a compress. Therefore, it is believed that the putty caulk composition of the present invention has other uses outside the dental applications. It is contemplated that the putty caulk composition of the present invention may be used wherever tissue needs to be isolated.

From the foregoing, it will be appreciated the present invention provides improved compositions and methods for repairing, sealing or otherwise isolating tissue and dental apparatus from harmful contact or irritation. The putty caulk compositions within the scope of the present invention not only act to repair and seal artificial instruments and apparatus, but also provide for the isolation of the same from natural tissue.

During dental procedures, it is often necessary to isolate certain tissue from other tissue or objects. In order to do so, for example, as illustrated in FIG. 1, base 23 of a tooth or crown 11 is prepared with a bead 24 or amount of putty caulk 12 to operate as a sealing seat for a thereafter placed dental or rubber dam. FIG. 2 shows rubber dam 10 in place around a tooth or crown 11 to which tooth or crown 11 strong peroxides are applied in vital bleaching, or hydrofluoric acid is used in porcelain etching. Such substances are very harmful to soft gingival tissue.

In order to adequately seal rubber dam 10 to a tooth or crown 11 or other dental prosthesis, putty caulk composition 12 can also be efficiently and accurately delivered around base 23 of tooth or crown 11 in a bead so as to fill in any gaps, voids, or other irregularities 13 between rubber dam 10 and base 23 of tooth or crown 11.

FIG. 2 illustrates the delivery of putty caulk composition 12 via a syringe 18 after rubber dam 10 has been put in place. However, a bead of putty caulk composition 12 may also be applied to base 23 of tooth or crown 11 prior to the placement of rubber dam 10. In this way, a subsequent bead of putty caulk composition 12, after dental or rubber dam 10 has been put in place, acts to form a superior seal or barrier at those points at which rubber dam 10 cannot be provided an effective seal.

It is just such an application in which the ability of putty caulk composition 12 to bond to itself and blend with a prior application of putty caulk 12 improves the art in providing an effective seal or barrier around base 23 of tooth or crown 11. This same procedure could be used at the base of any fixed dental prosthesis or orthodontic appliance.

After the relevant dental procedure is completed, removal of rubber dam 10 is accomplished and putty caulk composition 12 is quickly removed with a toothbrush, floss, or curette, and rinsed away.

Putty caulk composition 12 is also preferably used to assure a complete seal on the abutment tooth of a fixed bridge as shown in FIG. 5. After having placed rubber dam 10, and employing clamp 25 to draw rubber dam 10 as tightly over and around the fixed bridge as possible, with the aid of an explorer or a small blunt instrument, slip the instrument between rubber dam 10 and abutment 14. The dam is stretched away from the abutment long enough to allow a syringe to slip into the space between abutment 14 and the pontic.

Tip 19 of syringe 18 is placed in the proximity of the lingual portion of rubber dam 10. Putty caulk 12 is expressed into the void between the lingual and buccal aspects of rubber dam 10. Putty paste 12 is continuously expressed while withdrawing syringe 18. The result is an effective seal of putty paste composition 12 vertically and laterally having a connector for roof, rubber dam for two sides, abutment and pontic for the other two sides, and soft tissue for the floor.

The putty paste composition is also particularly useful when performing endodontics. As discussed above and shown in FIG. 1, a bead 24 of putty paste composition 12 may be placed around the tooth or teeth being isolated prior to placement of the rubber dam. A heavy bead may be needed to fill in areas of poor adaption. If putty caulk falls into pulpal cavity, it will not set hard, therefore, there is no need for concern of blocking the canal orifices or canals themselves.

As illustrated in FIG. 3, the preferred use of putty paste composition 12 is to repair an inadvertently torn or punctured rubber dam 15 adjacent to hard or soft, wet or dry tissue 20, or fixed dental prostheses. If during a dental procedure, rubber dam 10 becomes damaged by a tear adjacent to any tissue or prosthesis, tear 15 may be repaired by positioning syringe 18 between rubber dam 10 and the tissue and expressing putty caulk composition 12 around the perimeter of the hole. Thereafter, the remaining unsealed area of the hole may be filled with putty caulk composition 12. Putty caulk composition 12 may be shaped or contoured as needed.

The putty paste composition of the present invention is also preferably used to seal isolated holes 21 in rubber dams 10 not adjacent to supporting soft tissue 20, teeth 11, or other dental prosthesis 14. Hole or puncture 21 may be repaired by placing syringe 18 in the proximity of hole 21 and expressing putty caulk 12 around hole 21 in order to fill the hole. This may be accomplished with or without vacuuming rubber dam 10 to remove saliva and other fluids.

Several advantages to the dental professional are apparent. The dental professional need not stop the procedure, clean the area, remove the rubber dam, prepare the tissue, replace the rubber dam, and only thereafter continue the dental procedure. Instead, the dental professional may quickly, conveniently and efficiently seal the hole and continue with the procedure without waste of time and expense. Similarly, the wet and/or dry application of putty paste is of great convenience and practical use to the dental professional. Not only is the dental professional able to use readily available instruments or fingers to prepare the putty caulk, if necessary at all, and apply it to a wet and/or dry target area or tissue, but the application of the putty caulk does not require cleanup procedures.

The putty paste composition of the present invention can also be used as a bland bandage 22 to cover irritated areas 17 as illustrated in FIG. 4. A good example is lesioned, ulcerated, or cankered buccal tissue 17. For the purposes of the present invention, lesioned tissue may include diseased, aggravated, irritated, distressed, or otherwise ailing or sore tissue.

The putty paste composition may be applied in a number of ways. Putty caulk 12 may be applied directly to lesioned, ulcerated, or cankered tissue 17 and shaped and pressed to the desired shape or contour. In the alternative, an amount of the putty caulk may be expressed onto the tip of wet or dry finger. The putty caulk may then be rubbed, pressed, conformed to, or otherwise placed on lesioned, ulcerated, or cankered tissue 17 and formed to the desired shape.

Again, the wet and/or dry application of putty caulk is of practical use and convenience to the dental professional. The dental professional is able not only to use readily available instruments or fingers to prepare the putty caulk, if necessary at all, and apply it to a wet and/or dry target area or tissue, but the application of the putty caulk does not require careful and timely cleanup procedures.

It will be appreciated that the resulting properties and performance of the present invention provides for a putty caulk composition which is hydrophilic enough to attach to wet or dry tissue and hydrophobic enough to not wash away, whether that tissue to which it comes in contact is hard or soft.

Additionally, it will be appreciated that the present invention provides a putty caulk composition which has elastomeric properties which permit it to deform with the underlying tissue and resiliently retain its shape or form so as to remain a viable sealing, repairing or shielding material.

It will also be appreciated that great advantage is obtained because the present invention provides a putty caulk composition which will bond to itself. It may become necessary in the course of a dental procedure to readminister the caulk composition to the target area or tissue where some caulk still remains in place.

The caulk of the present invention does not set up in a state significantly different from the state in which it is administered. Therefore, the caulk composition remains fungible and readily accepts reapplication and additions of material at the same site. This offers an advantage to the dental professional because it is not necessary to stop other procedures and clean the site of a previous administration of the caulk composition. To the contrary, the dental professional may merely administer an addition amount of the caulk composition to the intended target area or tissue and then proceed with the dental procedure at hand.

Furthermore, it will be appreciated that the present invention results in a putty caulk composition that does not dry out or become brittle and loose its malleability and pliable nature. As a result, the compound of the present invention does not shrink or curl up at its edges and separate from the underlying tissue.

The present invention also results in a putty caulk composition which can be effectively applied under water, saliva and other fluids.

The present invention may be embodied in other specific forms without departing from the spirit or essential characteristics of the composition. The described embodiments are to be considered in all respects only as illustrative and not restrictive. The scope of the invention is, therefore, indicated by the appended claims rather then by the foregoing description. All changes which come within the meaning and range of equivalency of the claims are to be embraced within their scope.

What is claimed and desired to be secured by United States Letters Patent is:

1. A composition for repairing and sealing dental dams or other dental appliances in the mouth of a patient, the composition comprising:

a silicone-based material in an amount ranging from about 15% to about 60% by weight of the composition, wherein the silicone-based material provides to the composition sufficient properties of hydrophobicity and adhesion such that the composition is substantially insoluble in the aqueous environment of the mouth of the patient, while adhering to the dental dam or other dental appliance;

a lower weight aliphatic glycol in an amount up to about 60% by weight of the composition, wherein the glycol provides to the composition sufficient properties of hydrophilicity that the composition adheres to a moist dental dam or other dental appliance; and a cellulosic material in an amount ranging from about 10% to about 60% by weight of the composition, wherein the cellulosic material substantially maintains the homogeneity of the composition including the silicone-based material and the glycol.

2. A composition for repairing and sealing dental dams or other dental appliances in the mouth of the patient as defined in claim 1 further comprising a surfactant in an amount ranging from about 0.2% to about 10%, such that the homogeneity of the compound including the silicone-based material and the glycol is enhanced.

3. A composition for repairing and sealing dental dams or other dental appliances in the mouth of the patient as defined in claim 2, wherein the surfactant is a surfactant including polysorbate as an active ingredient.

4. A composition for repairing and sealing dental dams or other dental appliances in the mouth of the patient as defined in claim 3, wherein the polysorbate surfactant is in an amount ranging from about 1% to about 6% by weight of the composition.

5. A composition for repairing and sealing dental dams or other dental appliances in the mouth of the patient as defined in claim 2 further comprising an inert filler in an amount sufficient to increase the viscosity of the composition so that it is workable for its intended purpose.

6. A composition for repairing and sealing dental dams or other dental appliances in the mouth of the patient as defined in claim 5, wherein the inert filler comprises glass spheres.

7. A composition for repairing and sealing dental dams or other dental appliances in the mouth of the patient as defined in claim 6, wherein the size of the glass spheres range from about 1 micron to about 50 microns.

8. A composition for repairing and sealing dental dams or other dental appliances in the mouth of the patient as defined in claim 6, wherein the glass spheres are in an amount ranging from about 2% to about 15% by weight of the composition.

9. A composition for repairing and sealing dental dams or other dental appliances in the mouth of the patient as defined in claim 1, wherein the silicone-based material comprises polydimethylsiloxane.

10. A composition for repairing and sealing dental dams or other dental appliances in the mouth of the patient as defined in claim 9 wherein the polydimethylsiloxane is in an amount ranging from about 18% to about 36% by weight of the composition.

11. A composition for repairing and sealing dental dams or other dental appliances in the mouth of the patient as defined in claim 9 wherein the polydimethylsiloxane is in an amount ranging from about 20% to about 30% by weight of the composition.

12. A composition for repairing and sealing dental dams or other dental appliances in the mouth of the patient as defined in claim 1, wherein the lower weight aliphatic glycol comprises propylene glycol.

13. A composition for repairing and sealing dental dams or other dental appliances in the mouth of the patient as defined in claim 12 wherein the propylene glycol is in an amount ranging from about 18% to about 36% by weight of the composition.

14. A composition for repairing and sealing dental dams or other dental appliances in the mouth of the patient as defined in claim 12 wherein the propylene glycol is in an amount ranging from about 20% to about 30% by weight of the composition.

15. A composition for repairing and sealing dental dams or other dental appliances in the mouth of the patient as defined in claim 1, wherein the cellulosic material comprises carboxymethylcellulose.

16. A composition for repairing and sealing dental dams or other dental appliances in the mouth of the patient as defined in claim 10 wherein the carboxymethylcellulose is in an amount ranging from about 20% to about 55% by weight of the composition.

17. A composition for repairing and sealing dental dams or other dental appliances in the mouth of the patient as defined in claim 15 wherein the carboxymethylcellulose is in an amount ranging from about 33% to about 45% by weight of the composition.

18. A composition for repairing and sealing dental dams or other dental appliances in the mouth of the patient as defined in claim 1 wherein the moist dental dam or other dental appliance is submerged in saliva or other aqueous solutions.

19. A composition for repairing and sealing dental dams or other dental appliances in the mouth of the patient as defined in 1 wherein the silicone-based material comprises polydimethylsiloxane, and wherein the lower weight aliphatic glycol comprises propylene glycol.

20. A composition for repairing and sealing dental dams or other dental appliances in the mouth of the patient as defined in 19 wherein the polydimethylsiloxane is in an amount ranging from about 18% to about 36% by weight of the composition, and wherein the propylene glycol is in an amount ranging from about 18% to about 36% by weight of the composition such that when polydimethylsiloxane is present in a higher amount, propylene glycol is present in a lesser amount, and such that when propylene glycol is present in a higher amount, polydimethylsiloxane is present in a lesser amount.

21. A composition for repairing and sealing dental dams or other dental appliances in the mouth of the patient as defined in 19 wherein the polydimethylsiloxane is in an amount ranging from about 20% to about 30% by weight of the composition, and wherein the propylene glycol is in an amount ranging from about 20% to about 30% by weight of the composition such that when polydimethylsiloxane is present in a higher amount, propylene glycol is present in a lesser amount, and such that when propylene glycol is present in a higher amount, polydimethylsiloxane is present in a lesser amount.

22. A composition for repairing and sealing dental dams or other dental appliances in the mouth of the patient as defined in claim 1 wherein the silicone-based material comprises polydimethylsiloxane, wherein the low weight aliphatic glycol comprises propylene glycol, and wherein the cellulosic material comprises carboxymethylcellulose.

23. A composition for repairing and sealing dental dams or other dental appliances in the mouth of the patient as defined in 22 wherein the polydimethylsiloxane is in an amount ranging from about 18% to about 36% by weight of the composition, wherein the propylene glycol is in an amount ranging from about 18% to about 36% by weight of the composition, and wherein the carboxymethylcellulose is in an amount ranging from about 20% to about 55% by weight of the composition such that when polydimethylsiloxane is present in a higher amount, propylene glycol is present in a lesser amount, and such that when propylene glycol is present in a higher amount, polydimethylsiloxane is present in a lesser amount.

24. A composition for repairing and sealing dental dams or other dental appliances in the mouth of the patient as defined in 22 wherein the polydimethylsiloxane is in an amount ranging from about 20% to about 30% by weight of the composition, wherein the propylene glycol is in an amount ranging from about 20% to about 30% by weight of the composition, and wherein the carboxymethylcellulose is in an amount ranging from about 33% to about 45% by weight of the composition.

25. A composition for repairing and sealing dental dams or other dental appliances in the mouth of the patient as defined in claim 1 wherein the silicone-based material comprises polydimethylsiloxane, wherein the low weight aliphatic glycol comprises propylene glycol, wherein the cellulosic material comprises carboxymethylcellulose, and further comprises a surfactant including polysorbate as an active ingredient.

26. A composition for repairing and sealing dental dams or other dental appliances in the mouth of the patient as defined in 25 wherein the polydimethylsiloxane is in an amount ranging from about 18% to about 36% by weight of the composition, wherein the propylene glycol is in an amount ranging from about 18% to about 36% by weight of the composition, wherein the carboxymethylcellulose is in an amount ranging from about 20% to about 55% by weight of the composition, and wherein the polysorbate surfactant is in an amount ranging from about 0.2% to about 10.0% by weight of the composition.

27. A composition for repairing and sealing dental dams or other dental appliances in the mouth of the patient as defined in 25 wherein the polydimethylsiloxane is in an amount ranging from about 20% to about 30% by weight of the composition, wherein the propylene glycol is in an amount ranging from about 20% to about 30% by weight of the composition, wherein the carboxymethylcellulose is in an amount ranging from about 33% to about 45% by weight of the composition, and wherein the surfactant is in an amount ranging from about 1% to about 6% by weight of the composition.

28. A composition for repairing and sealing dental dams or other dental appliances in the mouth of a patient as defined in claim 1, wherein the silicone-based material is in an amount ranging from about 20% to about 35% by weight of the composition.

29. A composition for repairing and sealing dental dams or other dental appliances in the mouth of a patient as defined in claim 1, wherein the lower weight aliphatic glycol is in an amount ranging from about 20% to about 40% by weight of the composition.

30. A composition for repairing and sealing dental dams or other dental appliances in the mouth of a patient as defined in claim 1, wherein the cellulosic material is in an amount ranging from about 25% to about 35% by weight of the composition.

31. A composition for repairing and sealing dental dams or other dental appliances in the mouth of a patient, the composition comprising:
a silicone-based material in an amount ranging from about 15% to about 60% by weight of the composition, wherein the silicone-based material provides to the composition sufficient properties of hydrophobicity and adhesion such that the composition is substantially insoluble in the aqueous environment of the mouth of the patient, while adhering to the dental dam or other dental appliance;
a lower weight aliphatic glycol in an amount up to about 60% by weight of the composition, wherein the glycol provides to the composition sufficient properties of hydrophilicity that the composition adheres to a moist dental dam or other dental appliance;
a cellulosic material in an amount ranging from about 10% to about 60% by weight of the composition, wherein the cellulosic material substantially maintains the homogeneity of the composition including the silicone-based material and the glycol;
a surfactant in an amount ranging from about 0.2% to about 10% by weight of the composition, such that the homogeneity of the compound including the silicone-based material and the glycol is enhanced; and
an inert filler in an amount ranging from about 2% to about 15% by weight of the composition.

32. A composition for repairing and sealing dental dams and other dental appliances as defined in claim 28 wherein the silicone-based material comprises polydimethylsiloxane, wherein the low weight aliphatic glycol comprises propylene glycol, wherein the cellulosic material comprises carboxymethylcellulose, wherein the surfactant is a surfactant including polysorbate as an active ingredient, and wherein the inert filler comprises glass spheres.

33. A composition for repairing and sealing dental dams or other dental appliances in the mouth of the patient as defined in 32 wherein the polydimethylsiloxane is in an amount ranging from about 20% to about 30% by weight of the composition, wherein the propylene glycol is in an amount ranging from about 20% to about 30% by weight of the composition, wherein the carboxymethylcellulose is in an amount ranging from about 33% to about 45% by weight of the composition, wherein the polysorbate surfactant is in an amount ranging from about 1% to about 6% by weight of the composition, and wherein the glass spheres is in an amount ranging from about 4% to about 8% by weight of the composition such that when polydimethylsiloxane is present in a higher amount, propylene glycol is present in a lesser amount, and such that when propylene glycol is present in a higher amount, polydimethylsiloxane is present in a lesser amount.

34. A composition for isolating tissue from harmful contact or irritation, the composition comprising:
a silicone-based material in an amount ranging from about 15% to about 60% by weight of the composition, wherein the silicone-based material provides to the composition sufficient properties of hydrophobicity and adhesion such that the composition is substantially insoluble when inundated by aqueous solution, while adhering to tissue and isolating it from harmful contact or irritation;
a lower weight aliphatic glycol in an amount up to about 60% by weight of the composition, wherein the glycol provides to the composition sufficient properties of hydrophilicity such that the composition adheres to moist tissue to isolate it from harmful contact or irritation; and
a cellulosic material in an amount ranging from about 10% to about 60% by weight of the composition, wherein the cellulosic material substantially maintains the homogeneity of the composition including the silicone-based material and the glycol.

35. A composition for isolating tissue from harmful contact or irritation as defined in claim 34 further comprising a surfactant in an amount ranging from about 0.2% to about 10%, such that homogeneity the composition including the silicone-based material and the glycol is enhanced.

36. A composition for isolating tissue from harmful contact or irritation as defined in claim 35 wherein the surfactant is a surfactant including polysorbate as an active ingredient in an amount ranging from about 1% to about 6% by weight of the composition.

37. A composition for isolating tissue from harmful contact or irritation as defined in claim 35 further comprising an inert filler in an amount sufficient to increase the viscosity of the composition so that it is workable for its intended purpose.

38. A composition for isolating tissue from harmful contact or irritation as defined in claim 34, wherein the silicone-based material comprises polydimethylsiloxane.

39. A composition for isolating tissue from harmful contact or irritation as defined in claim 38 wherein the polydimethylsiloxane is in an amount ranging from about 20% to about 30% by weight of the composition.

40. A composition for isolating tissue from harmful contact or irritation as defined in claim 34, wherein the lower weight aliphatic glycol is propylene glycol.

41. A composition for isolating tissue from harmful contact or irritation as defined in claim 40 wherein the propylene glycol is in an amount ranging from about 20% to about 30% by weight of the composition.

42. A composition for isolating tissue from harmful contact or irritation as defined in claim 34 wherein the cellulosic material comprises carboxymethylcellulose.

43. A composition for isolating tissue from harmful contact or irritation as defined in claim 42 wherein the carboxymethylcellulose is in an amount ranging from about 33% to about 45% by weight of the composition.

44. A composition for isolating tissue from harmful contact or irritation as defined in claim 34 wherein the tissue is oral tissue in the mouth of the patient.

45. A composition for isolating tissue from harmful contact or irritation as defined in claim 34 wherein the tissue is oral tissue in the mouth of the patient including epithelial tissue to isolate lesioned tissue.

46. A composition for isolating tissue from harmful contact or irritation as defined in claim 34 wherein the tissue is epidermal tissue.

47. A composition for isolating tissue from harmful contact or irritation as defined in claim 34, wherein the silicone-based material is in an amount ranging from about 20% to about 35% by weight of the composition.

48. A composition for isolating tissue from harmful contact or irritation as defined in claim 34, wherein the lower weight aliphatic glycol is in an amount ranging from about 20% to about 40% by weight of the composition.

49. A composition for isolating tissue from harmful contact or irritation as defined in claim 34, wherein the cellulosic material is in an amount ranging from about 25% to about 35% by weight of the composition.

50. A method for adhering a protective dental caulking composition to wet or dry tissues and dental appliances so as to isolate tissue from harmful contact or irritation, the method comprising the steps of:
    (a) obtaining a dental caulking composition comprising
        (i) a silicone-based material present in an amount ranging from about 15% to about 60% by weight of the composition, wherein the silicone-based material provides the composition sufficient properties of hydrophobicity and adhesion such that it is substantially insoluble when inundated by aqueous solution, while adhering to a contact surface;
        (ii) a lower weight aliphatic glycol in an amount up to about 60% by weight of the composition, wherein the glycol provides the composition sufficient properties of hydrophilicity such that the composition adheres to a moist contact surface; and
        (iii) a cellulosic material in an amount ranging from about 10% to about 60% by weight of the composition, wherein the composition is homogeneously provided with sufficient hydrophobic properties such that the composition is substantially insoluble while resisting being washed away by aqueous solution, with sufficient adhesive properties such that the composition is capable of adhering to tissue and to dental appliances, and with sufficient hydrophilic properties such that the composition is capable of adhering to dry and to moist contact surfaces;
    (b) delivering and adhering a quantity of the composition to either the wet or dry contact surface, the composition having elastomeric properties which permit the composition to deform with the underlying contact surface; and
    (c) conforming the composition to the contact surface such that a tissue barrier is formed.

51. A method for isolating tissue from harmful contact or irritation as defined in claim 50 further comprising the step of delivering and conforming a second quantity of the composition to a quantity previously delivered and conformed to the contact surface.

52. A method for isolating tissue from harmful contact or irritation as defined in claim 50, wherein the composition is delivered and conformed to a moist contact surface in the mouth submerged under an aqueous solution.

53. A method for isolating tissue from harmful contact or irritation as defined in claim 52, wherein the aqueous solution comprises fluid used in dental procedures.

54. A method for isolating tissue from harmful contact or irritation as defined in claim 52, wherein the aqueous solution comprises saliva.

55. A method for isolating tissue from harmful contact or irritation as defined in claim 50, wherein the contact surface comprises a dental dam such that delivering and conforming the composition to the surface of the dental dam repairs a damaged dental dam.

56. A method for isolating tissue from harmful contact or irritation as defined in claim 50, wherein the contact surface comprises a dental dam such that delivering and conforming the composition to the surface of the dental dam forms a seal such that the tissue is isolated from harmful contact or irritation.

57. A method for isolating tissue from harmful contact or irritation as defined in claim 50, wherein the contact surface comprises tissue such that delivering and conforming the composition to the surface of the tissue forms a seal such that the tissue is isolated from harmful contact or irritation.

58. A method of isolating tissue from harmful contact or irritation as defined in claim 57, wherein the contact surface further comprises adjacent dental dams or other dental appliances such that delivering and conforming the composition to the surface of the tissue and dental dam or other dental appliance seals voids between the tissue and the dental dam or other dental appliance resulting in isolating the tissue from harmful contact or irritation.

59. A method of isolating tissue from harmful contact or irritation as defined in claim 57, wherein the contact surface further comprises adjacent dental dams or other dental appliances such that delivering and conforming the composition to the surface of the tissue and dental dam or other dental appliance forms a barrier between the tissue and the dental dam or other dental appliance.

60. A method of isolating tissue from harmful contact or irritation as defined in claim 50, wherein delivery of the composition to the contact surface is accomplished by employing a syringe.

* * * * *

UNITED STATES PATENT AND TRADEMARK OFFICE
CERTIFICATE OF CORRECTION

Page 1 of 2

PATENT NO. : 5,098,299

DATED : March 24, 1992

INVENTOR(S) : DAN E. FISCHER

It is certified that error appears in the above-identified patent and that said Letters Patent is hereby corrected as shown below:

Column 2, line 7, "prostheses" should be --prosthesis--
Column 3, line 44, "dental object" should be --dental objects--
Column 4, line 9, "loose" should be --lose--
Column 4, line 13, "looses" should be --loses--
Column 4, line 18, "coating pastes" should be --coating paste--
Column 4, line 31, "principle feature" should be --principal feature--
Column 4, line 33, "in appliances" should be --or appliances--
Column 4, line 64, "effecting" should be --affecting--
Column 5, line 28, after "be" insert --a--
Column 5, line 29, "a compositions" should be --a composition--
Column 5, line 35, "require" should be --requires--
Column 12, line 60, delete "a"
Column 13, line 15, delete "in"
Column 13, line 24, "agents" should be --agent--
Column 22, line 63, "hard," should be --hard;--
Column 24, line 18, "addition" should be --additional--
Column 24, line 23, "loose" should be --lose--
Column 26, line 64, "22" should be --claim 22--
Column 27, line 14, "25" should be --claim 25--
Column 27, line 26, "25" should be --claim 25--
Column 28, line 22, "32" should be --claim 32--
Column 28, line 31, "spheres is" should be --spheres are--

UNITED STATES PATENT AND TRADEMARK OFFICE
CERTIFICATE OF CORRECTION

PATENT NO. : 5,098,299

DATED : March 24, 1992

INVENTOR(S) : DAN E. FISCHER

It is certified that error appears in the above-identified patent and that said Letters Patent is hereby corrected as shown below:

Column 28, line 62, after "homogeneity" insert --of--

Signed and Sealed this

Twenty-first Day of September, 1993

Attest:

BRUCE LEHMAN

Attesting Officer

Commissioner of Patents and Trademarks